US012591975B2

(12) United States Patent
Saikou

(10) Patent No.: US 12,591,975 B2
(45) Date of Patent: Mar. 31, 2026

(54) IMAGE PROCESSING DEVICE, IMAGE PROCESSING METHOD, AND STORAGE MEDIUM

(71) Applicant: NEC Corporation, Tokyo (JP)

(72) Inventor: Masahiro Saikou, Tokyo (JP)

(73) Assignee: NEC CORPORATION, Tokyo (JP)

( * ) Notice: Subject to any disclaimer, the term of this patent is extended or adjusted under 35 U.S.C. 154(b) by 286 days.

(21) Appl. No.: 18/279,497

(22) PCT Filed: Mar. 1, 2021

(86) PCT No.: PCT/JP2021/007668
§ 371 (c)(1),
(2) Date: Aug. 30, 2023

(87) PCT Pub. No.: WO2022/185369
PCT Pub. Date: Sep. 9, 2022

(65) Prior Publication Data
US 2024/0153090 A1     May 9, 2024

(51) Int. Cl.
*G06T 7/00*          (2017.01)
*A61B 1/00*          (2006.01)
(Continued)

(52) U.S. Cl.
CPC ...... *G06T 7/0016* (2013.01); *A61B 1/000094* (2022.02); *G06T 7/11* (2017.01);
(Continued)

(58) Field of Classification Search
CPC ................................................ A61B 1/000094
See application file for complete search history.

(56) References Cited

U.S. PATENT DOCUMENTS 8,363,962 B2 *   1/2013   Nishimura ............ G06T 7/0002
                                                     382/128
8,600,134 B2 *  12/2013   Vercauteren .............. G06T 5/50
                                                     382/128
(Continued)

FOREIGN PATENT DOCUMENTS

JP        2008-036028 A       2/2008
JP        2009-050321 A       3/2009
(Continued)

OTHER PUBLICATIONS

JP Office Action for JP Application No. 2023-503539, mailed on Nov. 26, 2024 with English Translation.
(Continued)

*Primary Examiner* — Edward Park
(74) *Attorney, Agent, or Firm* — Sughrue Mion, PLLC

(57) ABSTRACT

The image processing device 1X includes a classification means 31X, an image selection means 33X, and a region extraction means 34X. The classification means 31X classifies each captured image acquired in time series by photographing an inspection target by a photographing unit provided in an endoscope, according to whether or not the each captured image includes an attention part to be paid attention to. The image selection means 33X selects a target image to be subjected to extraction of a region of the attention part from the each captured image, based on a result of the classification. The region extraction means 34X extracts the area of the attention part from the target image. The image processing device can support decision-making based on based on images captured by the endoscope.

19 Claims, 11 Drawing Sheets

100 : ENDOSCOPIC INSPECTION SYSTEM

(51) Int. Cl.

| | |
|---|---|
| *G06T 7/11* | (2017.01) |
| *G06V 10/40* | (2022.01) |
| *G06V 10/74* | (2022.01) |
| *G06V 10/764* | (2022.01) |
| *G16H 30/20* | (2018.01) |
| *G16H 30/40* | (2018.01) |

(52) U.S. Cl.

CPC ............ *G06V 10/40* (2022.01); *G06V 10/761* (2022.01); *G06V 10/764* (2022.01); *G16H 30/20* (2018.01); *G16H 30/40* (2018.01); *G06T 2207/10016* (2013.01); *G06T 2207/10068* (2013.01); *G06T 2207/20084* (2013.01); *G06T 2207/30096* (2013.01); *G06V 2201/03* (2022.01)

(56) References Cited

U.S. PATENT DOCUMENTS

| | | | | |
|---|---|---|---|---|
| 9,100,572 | B2 * | 8/2015 | Rodriguez-Serrano | ...................... G06V 20/584 |
| 9,672,608 | B2 * | 6/2017 | Hamada | .................... G06T 5/50 |
| 2007/0195165 | A1 | 8/2007 | Hirakawa | |
| 2008/0039692 | A1 | 2/2008 | Hirakawa | |
| 2008/0212881 | A1 | 9/2008 | Hirakawa | |
| 2009/0051695 | A1 | 2/2009 | Matsuda | |
| 2011/0206250 | A1 * | 8/2011 | McGinnis | ............. G06T 7/0012 382/128 |
| 2012/0113239 | A1 | 5/2012 | Krupnik et al. | |
| 2012/0316421 | A1 | 12/2012 | Kumar et al. | |
| 2016/0035352 | A1 * | 2/2016 | Furumoto | ............... G06F 3/167 704/276 |
| 2016/0100823 | A1 * | 4/2016 | Brandl | .................... H04N 23/80 382/131 |
| 2016/0379363 | A1 | 12/2016 | Kitamura et al. | |
| 2019/0156483 | A1 | 5/2019 | Kono et al. | |
| 2020/0074629 | A1 | 3/2020 | Zur | |
| 2020/0337537 | A1 | 10/2020 | Hirasawa et al. | |
| 2021/0118145 | A1 | 4/2021 | Shiratani | |
| 2021/0361142 | A1 | 11/2021 | Kitamura et al. | |
| 2022/0095889 | A1 | 3/2022 | Sato | |

FOREIGN PATENT DOCUMENTS

| | | | |
|---|---|---|---|
| JP | 2015-173827 | A | 10/2015 |
| JP | 2020-073081 | A | 5/2020 |
| WO | 2006/123455 | A1 | 11/2006 |
| WO | 2018/020558 | A1 | 2/2018 |
| WO | 2020/003607 | A1 | 1/2020 |
| WO | 2020/026349 | A1 | 2/2020 |
| WO | 2020/165978 | A1 | 8/2020 |
| WO | 2021/014584 | A1 | 1/2021 |

OTHER PUBLICATIONS

International Search Report for PCT Application No. PCT/JP2021/007668, mailed on May 18, 2021.

Extended European Search Report for EP Application No. 21928947.7, dated on Mar. 27, 2024.

* cited by examiner

100 : ENDOSCOPIC INSPECTION SYSTEM

CAPTURED
IMAGE

BINARY CLASSIFICATION
MODEL

INPUT

FEATURE
EXTRACTOR

SCORE
CALCULATOR

OUTPUT

CONFIDENCE
SCORE
OF PRESENCE OF
LESION PART
IS 0. 9

CONFIDENCE
SCORE
OF ABSENCE OF
LESION PART
IS 0. 1

CAPTURED
IMAGE

INPUT     SEGMENTATION MODEL     OUTPUT

MASK IMAGE

FIG. 4

CASE OF N = 3

DIFFERENCE IN CONFIDENCE SCORES REGARDING PRESENCE OF LESION PART IS SMALLER THAN t2
⇒CAPTURED IMAGE AT TIME T IS SELECTED AS SEGMENTATION TARGET IMAGE

: CONFIDENCE SCORE REGARDING PRESENCE OF LESION PART IS SMALLER THAN t1

: CONFIDENCE SCORE REGARDING PRESENCE OF LESION PART IS t1 OR MORE

FIG. 6

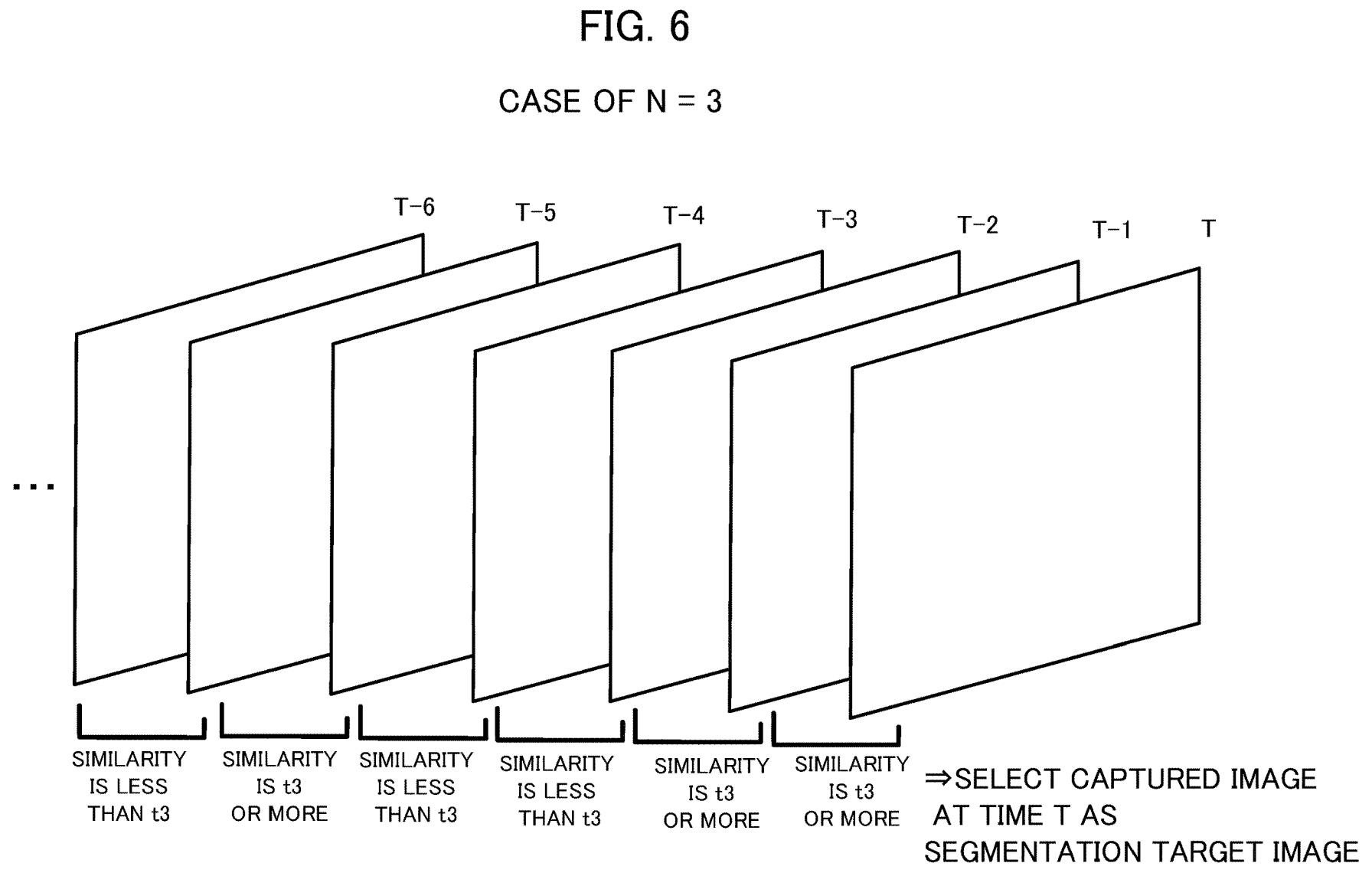

CASE OF N = 3

⇒SELECT CAPTURED IMAGE AT TIME T AS SEGMENTATION TARGET IMAGE

SIMILARITY IS t3 OR MORE

SIMILARITY IS t3 OR MORE

SIMILARITY IS LESS THAN t3

SIMILARITY IS LESS THAN t3

SIMILARITY IS t3 OR MORE

SIMILARITY IS LESS THAN t3

IMAGE PROCESSING DEVICE, IMAGE PROCESSING METHOD, AND STORAGE MEDIUM

This application is a National Stage Entry of PCT/JP2021/007668 filed on Mar. 1, 2021, the contents of all of which are incorporated herein by reference, in their entirety.

TECHNICAL FIELD

The present disclosure relates to a technical field of an image processing device, an image processing method, and storage medium for processing images acquired in endoscopic inspection.

BACKGROUND

An endoscopic system for displaying images taken in the lumen of an organ is known. For example, Patent Literature 1 discloses a learning method of a learning model configured to output information relating to a lesion part included in a captured image data when the captured image data generated by the photographing device is inputted.

CITATION LIST

Patent Literature

Patent Literature 1: WO2020/003607

SUMMARY

Problem to be Solved

When a trained model is used to detect a lesion part region from the image taken in the endoscopic inspection, there is an issue that it takes longer processing time to extract the lesion part region than the image acquisition interval and that the higher the accuracy of a model is, the more difficult the real-time processing by using the model becomes.

In view of the above-described issue, it is therefore an example object of the present disclosure to provide an image processing device, an image processing method, and a storage medium capable of extracting a region of an attention part such as a lesion part from an image captured in an endoscopic inspection.

Means for Solving the Problem

One mode of the image processing device is an image processing device including:

a classification means configured to classify each captured image acquired in time series by photographing an inspection target by a photographing unit provided in an endoscope, according to whether or not the each captured image includes an attention part to be paid attention to;

an image selection means configured to select a target image to be subjected to extraction of a region of the attention part from the each captured image, based on a result of the classification; and a region extraction means configured to extract the region of the attention part from the target image.

One mode of the image processing method is an image processing method executed by a computer, the image processing method including:

classifying each captured image acquired in time series by photographing an inspection target by a photographing unit provided in an endoscope, according to whether or not the each captured image includes an attention part to be paid attention to;

selecting a target image to be subjected to extraction of a region of the attention part from the each captured image, based on a result of the classification; and extracting the region of the attention part from the target image.

One mode of the storage medium is a storage medium storing a program executed by a computer, the program causing the computer to:

classify each captured image acquired in time series by photographing an inspection target by a photographing unit provided in an endoscope, according to whether or not the each captured image includes an attention part to be paid attention to;

select a target image to be subjected to extraction of a region of the attention part from the each captured image, based on a result of the classification; and extract the region of the attention part from the target image.

Effect

An example advantage according to the present invention is to suitably extract a region of an attention part from an endoscopic image.

BRIEF DESCRIPTION OF THE DRAWINGS

FIG. 4 It is a functional block diagram of the image processing device.

FIG. 6 It is a schematic diagram of a method of selecting a segmentation target image based on a feature vector.

EXAMPLE EMBODIMENTS

Hereinafter, example embodiments of an image processing device, an image processing method, and a storage medium will be described with reference to the drawings.

First Example Embodiment

(1) System Configuration

Figure 1:
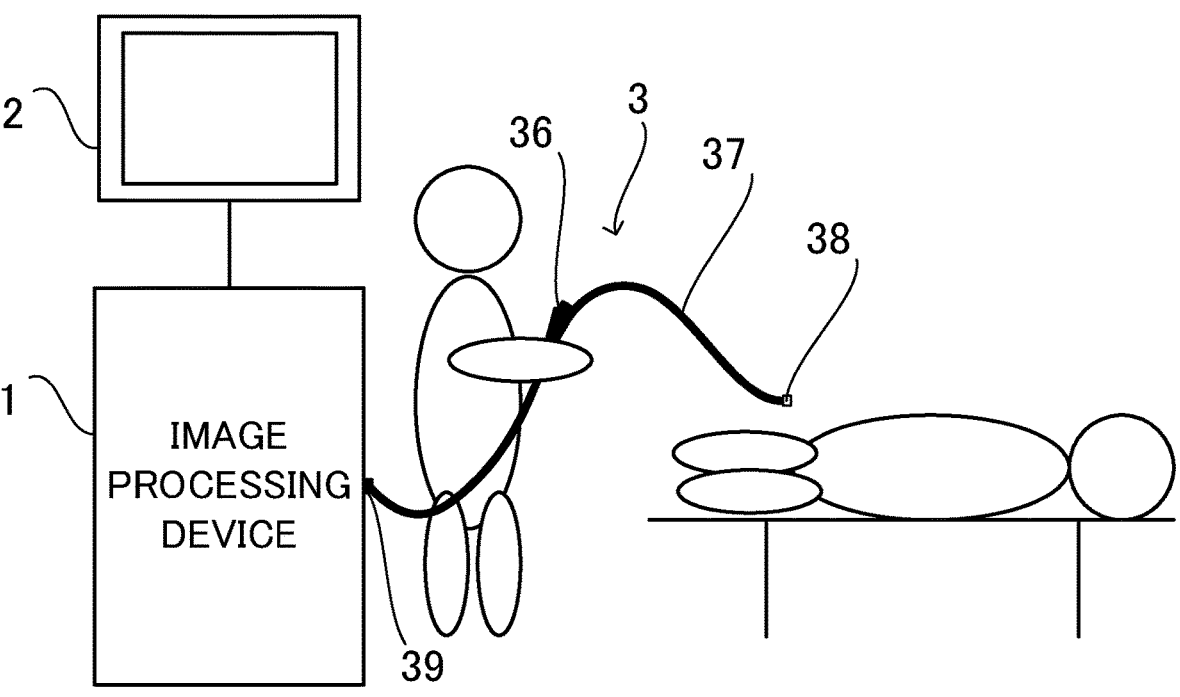
FIG. 1 It illustrates a schematic configuration of an endoscopic inspection system.

FIG. 1 shows a schematic configuration of an endoscopic inspection system 100. As shown in FIG. 1, the endoscopic inspection system 100 is a system for presenting a suspected part (a lesion part) of a lesion to an inspector such as a doctor who performs inspection or treatment using an endoscope, and mainly includes an image processing device 1, a display device 2, and an endoscope scope 3 connected to the image processing device 1.

The image processing device 1 acquires an image (also referred to as "captured image Ia") captured by the endo-scope 3 in time series from the endoscope 3 and displays a screen image based on the captured image Ia on the display device 2. The captured image Ia is an image to be captured at predetermined time intervals in at least one of the inser-tion process of the endoscope 3 to the subject or the ejection process of the endoscope 3 from the subject. In the present example embodiment, the image processing device 1 ana-lyzes the captured image Ia to extract a region (also referred to as "lesion image region") corresponding to a lesion part from the captured image Ia and display the information regarding the extracted lesion image region on the display device 2.

The display device 2 is a display or the like for displaying information based on the display signal supplied from the image processing device 1.

The endoscope 3 mainly includes an operation unit 36 for inspector to perform a predetermined input, a shaft 37 which has flexibility and which is inserted into the organ to be photographed of the subject, a pointed end unit 38 having a built-in photographing unit such as an ultra-small image pickup device, and a connecting unit 39 for connecting to the image processing device 1.

In the following description, as a representative example, the process in the endoscopic inspection of a large bowel will be described, but the inspection target may be not only the large bowel but also an esophagus or a stomach. Examples of the target endoscope in the present disclosure include a laryngendoscope, a bronchoscope, an upper diges-tive tube endoscope, a duodenum endoscope, a small bowel endoscope, a large bowel endoscope, a capsule endoscope, a thoracoscope, a laparoscope, a cystoscope, a cholangio-scope, an arthroscope, a spinal endoscope, a blood vessel endoscope, and an epidural endoscope. For example, the disease of a lesion part to be detected is exemplified as following (a) to (f).

- (a) Head and neck: pharyngeal cancer, malignant lym-phoma, papilloma
- (b) Esophagus: esophageal cancer, esophagitis, esopha-geal hiatal hernia, Barrett's esophagus, esophageal varices, esophageal achalasia, esophageal submucosal tumor, esophageal benign tumor
- (c) Stomach: gastric cancer, gastritis, gastric ulcer, gastric polyp, gastric tumor
- (d) Duodenum: duodenal cancer, duodenal ulcer, duodeni-tis, duodenal tumor, duodenal lymphoma
- (e) Small bowel: small bowel cancer, small bowel neo-plastic disease, small bowel inflammatory disease, small bowel vascular disease
- (f) Large bowel: colorectal cancer, colorectal neoplastic disease, colorectal inflammatory disease; colorectal polyps, colorectal polyposis, Crohn's disease, colitis, intestinal tuberculosis, hemorrhoids

(2) Hardware Configuration

Figure 2:
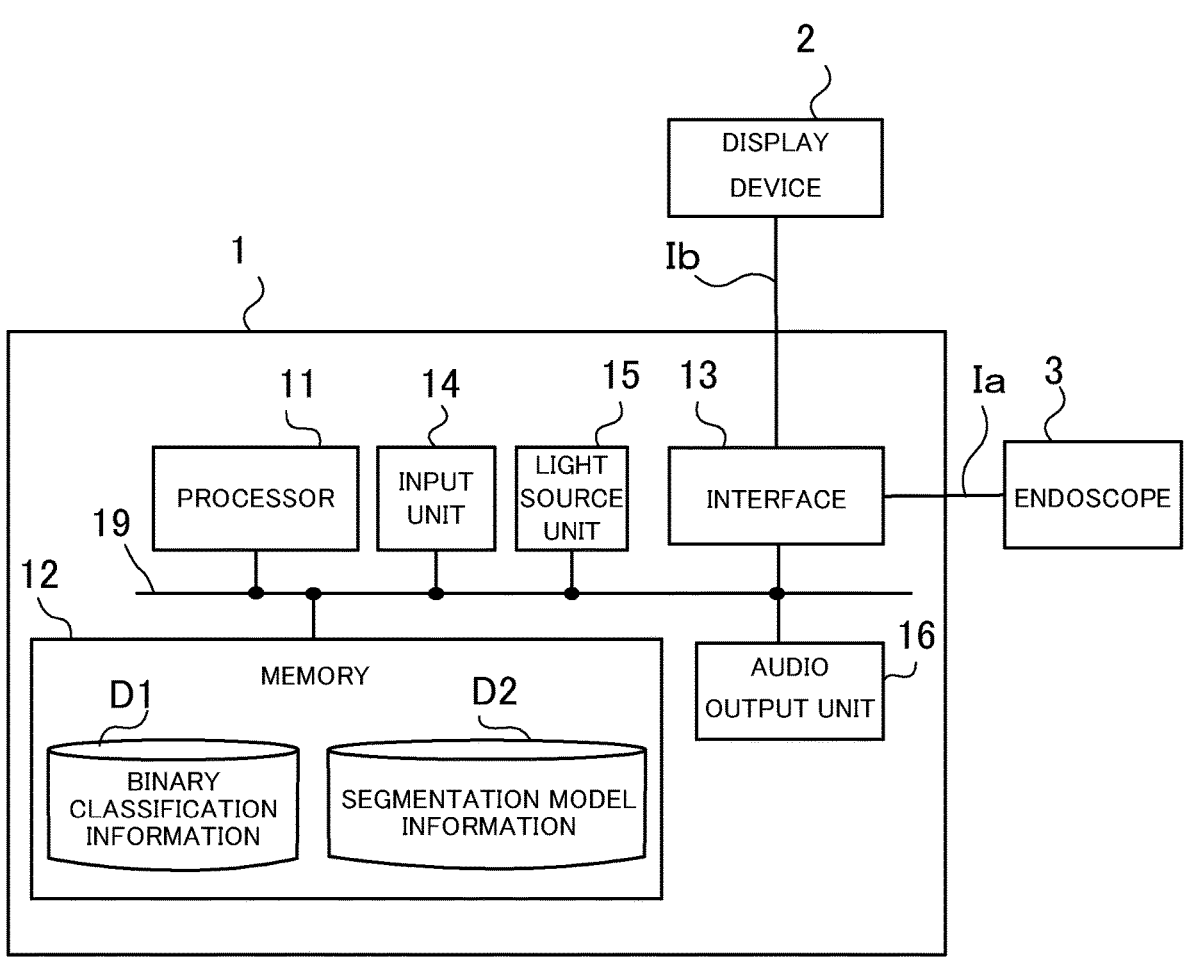
FIG. 2 It illustrates a hardware configuration of an image processing device.

FIG. 2 shows a hardware configuration of the image processing device 1. The image processing device 1 mainly includes a processing device 11, a memory 12, an interface 13, an input unit 14, a light source unit 15, and an audio output unit 16. Each of these elements is connected to one another via a data bus 19.

The processing device 11 executes a predetermined pro-cess by executing a program or the like stored in the memory 12. The processor 11 is a processor such as a CPU (Central Processing Unit), a GPU (Graphics Processing Unit), and a TPU (Tensor Processing Unit). The processor 11 may be configured by a plurality of processors. The processor 11 is an example of a computer.

The memory 12 is configured by various memories including volatile memories used as working memories and non-volatile memories for storing the information necessary for the image processing device 1, such as a RAM (Random Access Memory) and a ROM (Read Only Memory). The memory 12 may include an external storage device, such as a hard disk, that is connected to or embedded in the image processing device 1, or may include a storage medium, such as a removable flash memory. The memory 12 stores a program for the image processing device 1 to execute the process according to the present embodiment. The memory 12 also store binary classification model information D1 and the segmentation model information D2. The details of these data will be described later. At least one of the binary classification model information D1 and the segmentation model information D2 may be stored in an external device capable of is wired or wireless data communication with the image processing device 1, instead of being stored in the memory 12.

The interface 13 performs an interface operation between the image processing device 1 and an external device. For example, the interface 13 supplies the display information "Ib" generated by the processor 11 to the display device 2. Further, the interface 13 supplies the light generated by the light source unit 15 to the endoscope 3. The interface 13 also provides an electrical signal to the processor 11 indicative of the captured image Ia supplied from the endoscope 3. The interface 13 may be a communication interface, such as a network adapter, for wired or wireless communication with the external device, or a hardware interface compliant with a USB (Universal Serial Bus), a SATA (Serial AT Attach-ment), or the like.

The input unit 14 generates an input signal based on the operation by the inspector. Examples of the input unit 14 include a button, a touch panel, a remote controller, and a voice input device. The light source unit 15 generates light for supplying to the pointed end unit 38 of the endoscope 3. The light source unit 15 may also incorporate a pump or the like for delivering water and air to be supplied to the endoscope 3. The audio output unit 16 outputs a sound under the control of the processor 11.

(3) Data Overview

Next, a description will be given of the binary classifi-cation model information D1 and the segmentation model information D2.

The binary classification model information D1 is infor-mation regarding a binary classification model configured to output information regarding the classification according to whether or not the captured image Ia includes a lesion part. For example, the binary classification model information D1 includes parameters required to build (configure) the binary classification model. The binary classification model is an arbitrary machine learning model or a statistical model, and is a model configured to output information (classification information) as to whether or not a lesion part exists in the inputted captured image Ia when a captured image Ia is inputted thereto. The binary classification model may output a binary value (e.g., a value of 0 or 1) in accordance with whether or not a lesion part exists, or may output a set of a confidence score regarding the presence of a lesion part and a confidence score regarding the absence of a lesion part, or may output the both thereof. The term "confidence score regarding the presence of a lesion part" and "confidence score regarding the absence of a lesion part" correspond to the term "confidence score regarding the presence/absence of a lesion part" to be described later. In addition, the term "confidence score of the presence of a lesion part" indicates the degree of possibility that a lesion part exists in the captured image Ia", and increases with increase in the degree of possibility. The term "confidence score of the absence of a lesion part" indicates the degree of possibility that a lesion part does not exist in the captured image Ia", and increases with increase in the degree of possibility. The binary classification model is an example of a "classification model".

Figure 3A:
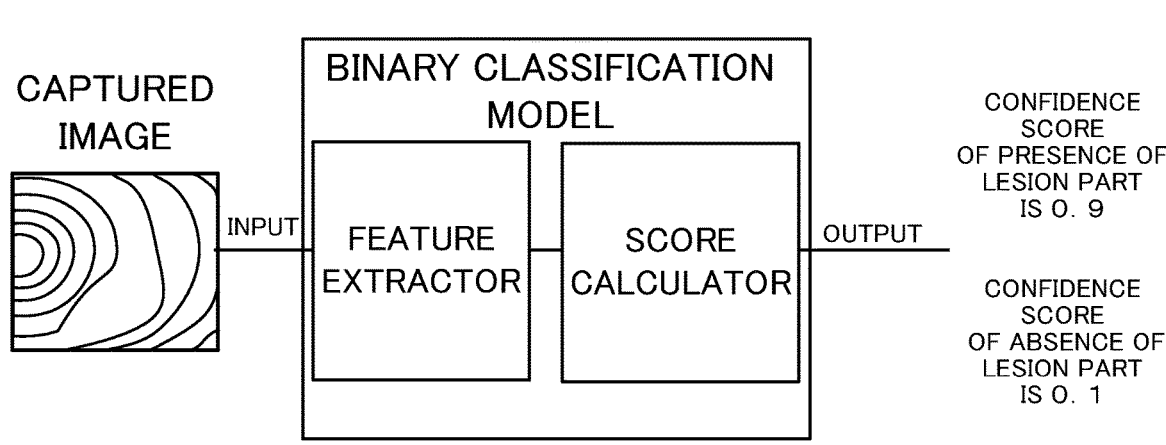
FIG. 3A is a schematic diagram of a binary classification model.

FIG. 3A is a schematic diagram of a binary classification model configured based on the binary classification model information D1. In FIG. 3A, the binary classification model has a feature extractor and a score calculator. The feature extractor extracts the feature with a predetermined dimension when a captured image Ia is inputted thereto, and supplies the feature vector representing the extracted feature to the score calculator. The score calculator outputs score(s) (in FIG. 3A, the confidence score of the presence of a lesion part and the confidence score of the absence of a lesion part) by inputting the feature vector supplied from the feature extractor.

The binary classification model may be, for example, a model based on logistic regression, k-neighborhood method, boosting, decision tree, neural network, support vector machine, or the like. Examples of the architecture of the neural network include a AlexNet, VGG, ResNet, SqueezeNet, DenseNet, Inception, GoogLeNet, ShuffleNet, MobileNet, ResNeXt, Wide ReNet, and NASNet. When the binary classification model is based on a neural network, the binary classification model information D1 includes various parameters such as a layer structure, a neuron structure of each layer, the number of filters and the size of filters in each layer, and the weight for each element of each filter.

The segmentation model information D2 is information regarding a segmentation model configured to extract a region (also referred to as "lesion image region Tc") of a lesion part from an inputted captured image Ia. The segmentation model informational D2 contains parameters required to build (configure) the segmentation model. The segmentation model is, for example, a machine-learning model, such as a neural network, configured to output an extraction result of the lesion image region Tc in the inputted captured image Ia when a captured image Ia is inputted thereto. Examples of the extraction result of the lesion image region Tc outputted by the segmentation model include a mask image (binary image in which the pixel value corresponding to the lesion image region Tc is different from the pixel value of the others) of the lesion image region Tc and a reliability map which is a map on the image showing the reliability of being the lesion image region Tc.

Figure 3B:
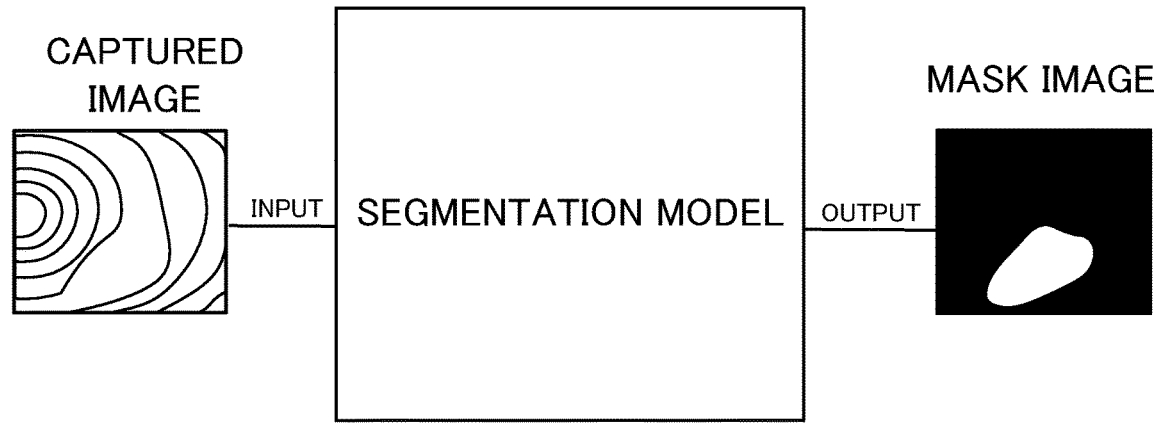
FIG. 3B is a schematic diagram of a segmentation model.

FIG. 3B is a schematic diagram of a segmentation model configured based on the segmentation model informational D2. In FIG. 3B, as an example, when the captured image Ia selected by the image processing device 1 is inputted to the segmentation model, the segmentation model outputs a mask image representing the lesion image region Tc in the input captured image Ia as the extraction result of the lesion image region Tc.

Examples of the typical neural network models used as the segmentation model include Fully Convolutional Network, SegNet, U-Net, V-Net, Feature Pyramid Network, Mask R-CNN, and DeepLab.

(4) Extraction and Display of Lesion Image Region

Next, a description will be given of the extracting and displaying related process of the lesion image region Tc to be executed by the image processing device 1. Schematically, the image processing device 1 applies the segmentation model to the captured image Ia that is selected based on the information outputted by the binary classification model, and causes the display device 2 to display the extracted result of the lesion image region Tc outputted by the segmentation model. Thus, the image processing device 1 performs extraction and presentation of highly accurate lesion image region Tc while suitably reducing the processing load.

Here, a supplementary description will be given of the relation between the binary classification model and the segmentation model. Since the binary classification model does not extract a lesion part, the processing burden of the binary classification model is lower than that of the segmentation model, and the processing time is within the interval based on the frame rate of captured images Ia. Thus, the binary classification model is suitable for real-time processing. On the other hand, since the segmentation model extracts the lesion part (i.e., determine the lesion image region Tc), the processing burden is higher than that of the binary classification model, and it tends to take a processing time longer than the interval based on the frame rate of captured images Ia. This tendency becomes more pronounced as the high-precision segmentation model is used. Therefore, when the segmentation model is applied to all captured images Ia, the processing load of the image processing device 1 becomes excessive and therefore real-time processing cannot be performed. In view of the above, in the present example embodiment, the binary classification model is applied to all captured images Ia while the segmentation model is selectively applied according to the information outputted by the binary classification model. Thus, the image processing device 1 extracts and presents the highly accurate lesion image region Tc while maintaining the real-time processing.

Figure 4:
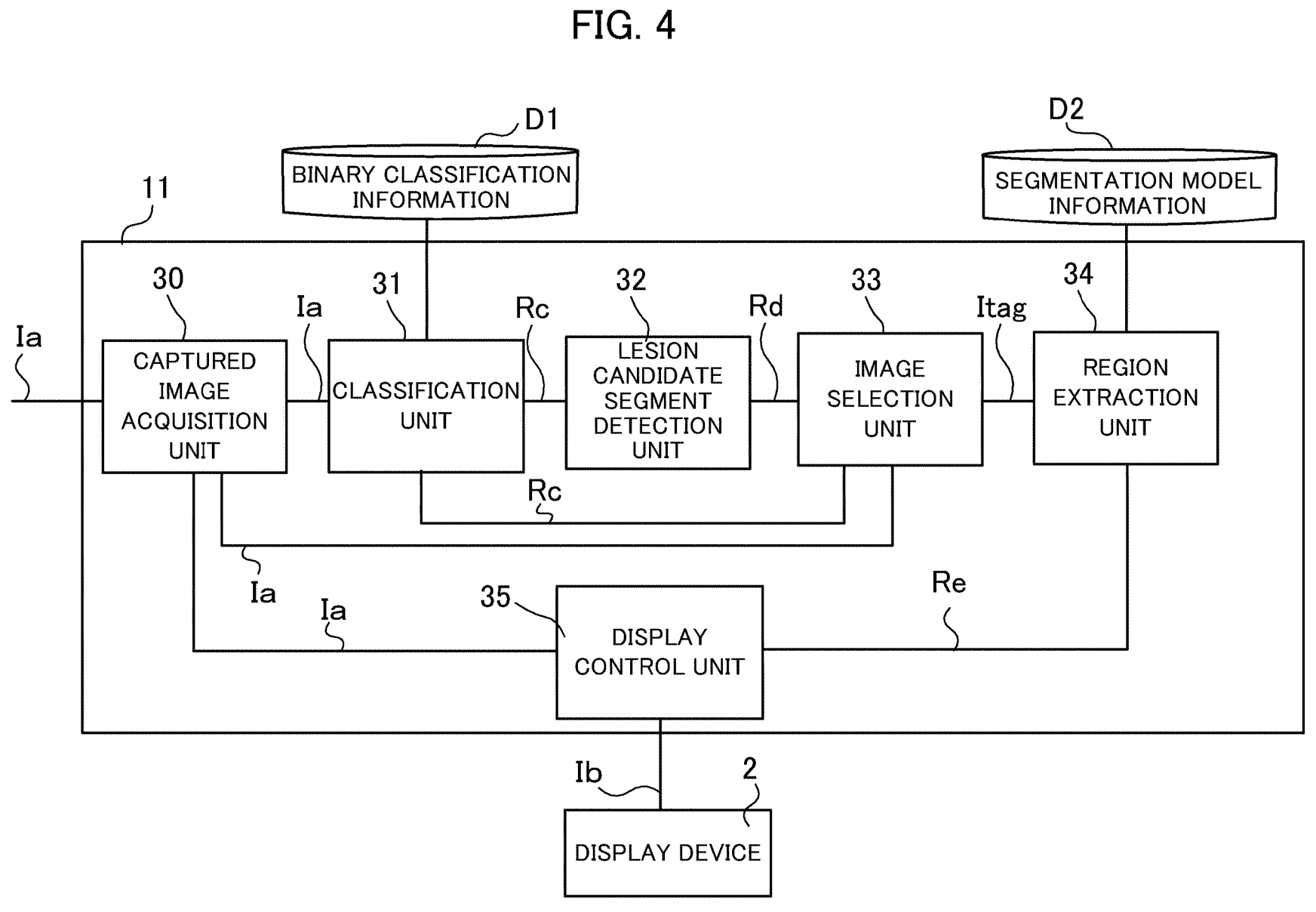

FIG. 4 is a functional block diagram of the image processing device 1. As shown in FIG. 4, the processer 11 of the image processing device 1 functionally includes a captured image acquisition unit 30, a classification unit 31, a lesion candidate segment detection unit 32, an image selection unit 33, a region extraction unit 34, and a display control unit 35. In FIG. 4, blocks to exchange data with each other are connected by a solid line, but the combination of the blocks to exchange data with each other is not limited to FIG. 4. The same applies to the drawings of other functional blocks described below.

The captured image acquisition unit 30 acquires a captured image Ia captured by the endoscope 3 via the interface 13 at predetermined intervals. Then, the captured image acquisition unit 30 supplies the acquired captured image Ia to the classification unit 31, the image selection unit 33, and the display control unit 35, respectively.

The classification unit 31 classifies each captured image Ia captured by the captured image acquisition unit 30 according to whether or not it includes a lesion part, and supplies the classification result "Rc" to the lesion candidate segment detection unit 32 and the image selection unit 33. In this instance, the classification unit 31 builds the binary classification model by referring to the binary classification model information D1, and acquires the classification result Rc by inputting the captured image Ia acquired by the captured image acquisition unit 30 to the built binary classification model. The classification unit 31 may include, in the classification result Rc to be supplied to the image selection unit 33, not only the confidence scores as to the presence and absence of the lesion part but also the feature vector that is outputted by the feature extractor of the binary classification model. The feature vector, as described later, is used for selecting the captured image Ia by the image selection unit 33.

The lesion candidate segment detection unit 32 detects, based on the classification result Rc for each captured image Ia supplied from the classification unit 31, a time segment (also referred to as "lesion candidate segment St") in which consecutive captured images Ia in time series classified as the presence of a lesion part are acquired. In this case, for example, if the newest captured image Ia is classified as an image including a lesion part (e.g., if the confidence score of the presence of the lesion part is higher than the confidence score of the absence of the lesion part), the lesion candidate segment detection unit 32 detects the lesion candidate segment St including the newest captured image Ia. On the other hand, if the newest captured image Ia is classified as an image which does not includes any lesion part in a period of the lesion candidate segment St being under detection, the lesion candidate segment detection unit 32 determines that the lesion candidate segment St has ended. Then, the lesion candidate segment detection unit 32 supplies the segment detection result "Rd" regarding the lesion candidate segment St to the image selection unit 33.

The image selection unit 33 selects an image (also referred to as "segmentation target image Itag") to which the segmentation model is to be applied from captured images Ia that belong to the lesion candidate segment St, on the basis of the classification result Rc and the segment detection result Rd. An approach for selecting segmentation target image Itag will be described later. The image selection unit 33 supplies the selected segmentation target image Itag to the region extraction unit 34

The region extraction unit 34 performs a process of extracting the lesion image region Tc from the segmentation target image Itag selected by the image selection unit 33. In this instance, the region extraction unit 34 acquires the extraction result of the lesion image region Tc by inputting the segmentation target image Itag into the segmentation model built based on the segmentation model information D2. Then, the region extraction unit 34 supplies the region extraction result "Re" regarding the lesion image region Tc to the display control unit 35.

The display control unit 35 generates display information Ib based on the captured image Ia and the region extraction result Re. Then, the display control unit 35 supplies the display information Ib to the display device 2 via the interface 13 to thereby cause the display device 2 to display information regarding the captured image Ia and the lesion image region Tc. The display example by the display control unit 35 will be described later.

Here, for example, each component of the captured image acquisition unit 30, the classification unit 31, the lesion candidate segment detection unit 32, the image selection unit 33, the region extraction unit 34 and the display control unit 35 can be realized by the processor 11 executing a program. In addition, the necessary program may be recorded in any non-volatile storage medium and installed as necessary to realize the respective components. In addition, at least a part of these components is not limited to being realized by a software program and may be realized by any combination of hardware, firmware, and software. At least some of these components may also be implemented using user-programmable integrated circuitry, such as FPGA (Field-Programmable Gate Array) and microcontrollers. In this case, the integrated circuit may be used to realize a program for configuring each of the above-described components. Further, at least a part of the components may be configured by a ASSP (Application Specific Standard Produce), ASIC (Application Specific Integrated Circuit) and/or a quantum processor (quantum computer control chip). In this way, each component may be implemented by a variety of hardware. The above is true for other example embodiments to be described later. Further, each of these components may be realized by the collaboration of a plurality of computers, for example, using cloud computing technology.

(5) Selection of Segmentation Target Image

Next, a description will be given of a method of selecting the segmentation target image Itag by the image selection unit 33 when the lesion candidate segment detection unit 32 detects the lesion candidate segment St. In order to select an image corresponding to a stable output duration of the binary classification model in the lesion candidate segment St, the image selection unit 33 selects the segmentation target image Itag on the basis of the classification result Rc of each captured image Ia in the lesion candidate segment St. By selecting an image corresponding to the stable output duration of the binary classification model as the segmentation target image Itag, the segmentation target image Itag with no or minor image blurring caused by the endoscopic operation by an inspector can be selected, for example. With this image selection, it is expected to extract highly accurate lesion image region Tc by the segmentation model. Further, on the basis of the above-described lesion image region Tc extracted with high accuracy, it is possible to present a suitable image as a display image to the inspector.

In the present exemplary example embodiment, if the condition regarding each classification result Rc of a predetermined number of captured images Ia is met consecutively in time series, the image selection unit 33 selects the segmentation target image Ia from the predetermined number of captured images Ic. This enables selection of a segmentation target image Itag with no or minor blurring image caused by endoscopic manipulation by an inspector. In this case, examples of the condition regarding the classification result Rc include a condition based on a confidence score regarding the presence/absence of a lesion part in the captured image Ia, and a condition based on the feature vector extracted from the captured image Ia. In this way, the image selection unit 33 may select the segmentation target image Itag based on the confidence score regarding the presence/absence of a lesion part in the captured image Ia, or may select the segmentation target image Itag based on the feature vector extracted from the captured image Ia. In the following, a method of selecting a segmentation target image Itag based on the confidence score regarding the presence/absence of a lesion part in the captured image Ia and a method of selecting the segmentation target image Itag based on the feature vector extracted from the captured image Ia will be described in order.

(5-1) Selection Method Based on Confidence Score

The image selecting unit 33 may determine whether or not to apply the segmentation model based on the confidence score regarding the presence/absence of a lesion part outputted by the binary classification model and select the segmentation target image Itag from the captured images Ia belonging to the lesion candidate segment St.

In this case, if there are a predetermined number "N" (N is an integer of 2 or more) of consecutive captured images Ia in which each confidence score regarding the presence of a lesion part is equal to or larger than a predetermined threshold value (also referred to as "first threshold value t1") and the difference in the confidence scores regarding the presence of the lesion part is smaller than a predetermined threshold value (also referred to as "second threshold value t2"), the image selection unit 33 determines that the applicable condition of the segmentation model is satisfied. Then, the image selection unit 33 selects, as the segmentation target image Itag, the Nth (i.e., most recent) captured image Ia among the N captured images Ia that satisfy the applicable condition of the segmentation model. The first threshold value t1, the second threshold value t2, and the number of frames N relating to the applicable condition of the segmentation model are predetermined in consideration of the classification accuracy of the binary classification model, for example, and are stored in advance in the memory 12 or the like.

Figure 5:
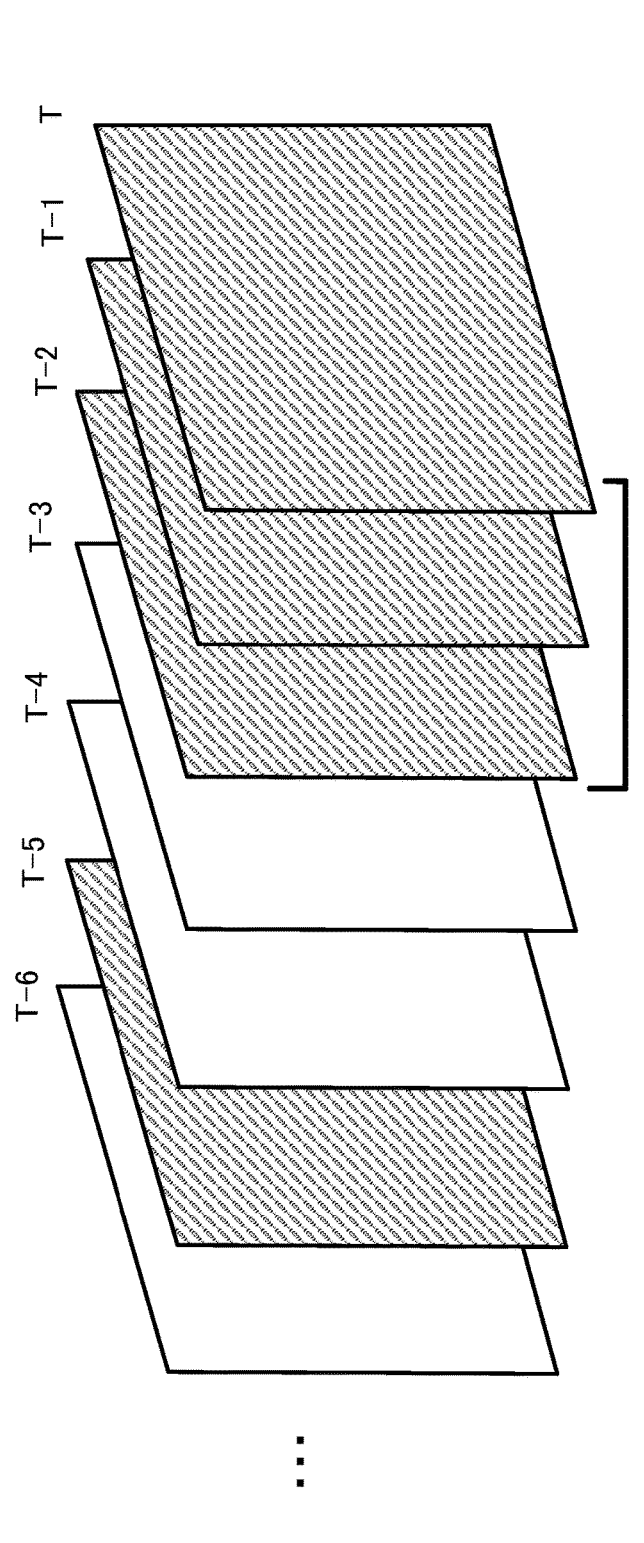
FIG. 5 It is a schematic diagram of a method of selecting a segmentation target image based on confidence score.

FIG. 5 is a schematic diagram showing a method of selecting the segmentation target image Itag based on the confidence score. In FIG. 5, the most recent captured image Ia acquired at the time "T" and the six captured image Ia acquired immediately before the most recently captured image Ia are displayed in association with the acquired times "T" to "T−6." In FIG. 5, captured images Ia in which each confidence score regarding the presence of a lesion part is equal to or larger than the first threshold value t1 are indicated with hatching. Here, the number of frames N is assumed to be set to "3".

In FIG. 5, for any of the captured image Ia acquired at time T, the captured image Ia acquired at time "T−1", and the captured image Ia acquired at time "T−2", the confidence score of the presence of a lesion part is equal to or larger than the first threshold value t1. In addition, the difference (i.e., the difference between the largest value and the smallest value of the confidence scores of the presence of a lesion part among these captured images Ia) in the confidence scores for these captured images Ia is smaller than the second threshold value t2. Since there are N consecutive captured images Ia in which each confidence score of the presence of a lesion part is equal to or larger than the first threshold value t1 and the difference in the confidence scores of the presence of a lesion part is less than the second threshold value t2, the image selection unit 33 selects the segmentation target image Itag to be the captured image Ia of the time T which is the Nth captured image Ia. Thus, the image selection unit 33 can suitably select the segmentation target image Itag that is the captured image Ia corresponding to a stable output duration of the binary classification model.

The captured image Ia acquired at the time "T−5" does not satisfy the applicable conditions of the segmentation model regarding the number of frames N, since the confidence scores of the presence of a lesion part of captured images Ia acquired just before and after the time "T−5" are less than the first threshold value t1, even though the confidence score of the presence of a lesion part is equal to or larger than the first threshold value t1. Therefore, the captured image Ia acquired at the time "T−5" is not selected as the segmentation target image Itag.

Here, some variations of the method of selecting the segmentation target image Itag based on the above-described confidence score will be described.

For example, the image selection unit 33 may adaptively change the number of frames N in accordance with the selection of the segmentation target image Itag. For example, after selecting the segmentation target image Itag in a certain subject candidate segment St, the image selection unit 33 increases the number of frames N of frames by a predetermined number in the subject candidate segment St. If the applicable conditions of the segmentation model after the increase in the number of frames N is satisfied, the image selection unit 33 reselects the segmentation target image Itag.

For example, in the example shown in FIG. 5, after selecting the captured image Ia at the time T as the segmentation target image Itag, the image selection unit 33 changes the number of frames N from "3" to "5." Then, the image selection unit 33 selects the captured image Ia acquired at the time "T+2" as the segmentation target image t1, when each confidence score regarding the presence of a lesion part of captured images Ia acquired at the time "T+1" and the time "T+2" is equal to or more than the first threshold value t2 and the difference in the confidence scores regarding the presence of a lesion part of captured images Ia acquired at the time T−2 to the time T+2 is less than the second threshold value t2. Thereafter, the segmentation target image Itag selected by the image selection unit 33 is supplied to the region extraction unit 34.

According to this example, the image selection unit 33 can additionally select the segmentation target image Itag in the lesion candidate segment St to suitably update the display relating to the lesion image region Tc to be displayed on the display device 2. On the other hand, the image selection unit 33 returns the number of frames N to the default value "3" when it is recognized that the most recently captured image Ia does not belong to the lesion candidate segment St on the basis of the segment detection result Rd generated by the lesion candidate segment detection unit 32.

The image selection unit 33 may change at least one of the first threshold value t1 or the second threshold value t2 in response to the increase in the number of frames N. For example, when increasing the number of frames N, the image selection unit 33 increases the first threshold value t1 by a predetermined value, or decreases the second threshold value t2 by a predetermined value. Thus, it is possible to adjust so that the segmentation target image Itag representing the same lesion part is less likely to be selected (i.e., the updating of the display regarding the lesion image region Tc is less likely to be performed). On the other hand, when decreasing the number of frames N, the image selection unit 33 decreases the first threshold value t1 by a predetermined value or increases the second threshold value t2 by a predetermined value. Thus, it is possible to adjust so that the segmentation target image Itag representing the same lesion part is easily selected (i.e., the updating of the display with respect to the lesion image region Tc is easily performed).

In another example of changing the number of frames N, the image selection unit 33 may set, to a value smaller than the default value, the number of frames N to be applied when the lesion candidate segment St is detected again immediately after the lesion candidate segment St has ended. For example, in the example shown in FIG. 5, the image selection unit 33 may set the number of frames N to a value smaller than the default value, if the lesion candidate segment St ended due to the confidence score regarding the presence of a lesion part of the captured image Ia acquired at time T+1 being lower than the first threshold value t1 and the lesion candidate segment St is detected again within a predetermined number of frames immediately thereafter. In this way, even when the confidence score regarding the presence of a lesion part is temporarily lowered due to the flicker in the image or the like, the image selection unit 33 can select the segmentation target image Itag at an early stage by reducing the number of frames N.

The image selection unit 33 may select the segmentation target image Itag from captured images Ia other than the Nth captured image Ia when the applicable condition of the segmentation model is satisfied. For example, the image selection unit 33 may select, as the segmentation target image Itag, the captured image Ia having the highest confidence score of the presence of a lesion part among the N captured images Ia which satisfies the applicable condition of the segmentation model.

(5-2) Selection Method Based on Feature Vector

Based on the feature vector outputted by the feature extractor of the binary classification model, the image selection unit 33 may determine whether or not to apply the segmentation model, and select the segmentation target image Itag from the captured images Ia which belong to the lesion candidate segment St.

For example, based on the inner product of the feature vectors of the two consecutive captured images Ia, the image selection unit 33 calculates the similarity (e.g., cosine similarity) of these captured images Ia. Then, the image selection unit 33 calculates the similarity for every pair of consecutive captured images selected from N consecutive captured images Ia. Then, if every similarity is equal to or larger than a predetermined threshold value (also referred to as "third threshold value t3"), the image selection unit 33 determines that the applicable condition of the segmentation model is satisfied. Then, the image selection unit 33 selects the Nth (i.e., most recent) captured image Ia from among them as the segmentation target image Itag.

FIG. 6 is a schematic diagram of a method of selecting the segmentation target image Itag based on feature vectors. In FIG. 6, in the same way as in FIG. 5, the most recently captured image Ia acquired at the time T and the six captured images Ia acquired at the time T−1 to time T−6 immediately before the captured image Ia at the time T are displayed in association with the acquired time. Here, the number of frames N is assumed to be set to "3".

In FIG. 6, the similarity based on the inner product of the feature vectors is calculated for every two consecutive captured image Ia. Then, the image selection unit 33 compares the calculated similarity with the third threshold value t3, and determines whether or not every similarity of the N (three in this case) consecutive captured images Ia is equal to or larger than the third threshold value t3. The image selection unit 33 determines that the applicable condition of the segmentation model is satisfied for the N consecutive captured images Ia acquired from the time T−2 to the time T, since the similarity between the captured images Ia acquired at the time T−2 and the time T−1 and the similarity between the captured images Ia acquired at the time T−1 and the time T are both equal to or larger than the third threshold value t3. Therefore, in this instance, the image selection unit 33 selects the captured image Ia acquired at time T as the segmentation target image Itag.

Even in this case, the image selection unit 33 can suitably select, as the segmentation target image Itag, the captured image Ia corresponding to a stable part where the output generated by the binary classification model is stable. As in the method of selecting the segmentation target image Itag based on the confidence score, the image selection unit 33 may adaptively change the number of frames N. Further, when increasing the number of frames N in accordance with the selection of the segmentation target image Itag, the image selection unit 33 may adjust the updating frequency of the lesion image region Tc by changing the third threshold value t3 in the same way. Instead of selecting the Nth captured image Ia as the segmentation target image Itag, the image selection unit 33 may select the segmentation target image Itag based on the confidence score from the N captured images Ia other than the Nth captured image Ia.

The image selection unit 33 may combine the method of selecting the segmentation target image Itag based on the confidence score and the method of selecting the segmentation target image Itag based on the feature vector. In this case, the image selection unit 33 selects the segmentation target image Itag when both of the applicable condition of the segmentation model based on the confidence score and the applicable condition of the segmentation model based on the feature vector are satisfied.

(6) Display Control

Next, a description will be given of the display control of the display device 2 to be executed by the display control unit 35.

Figure 7:
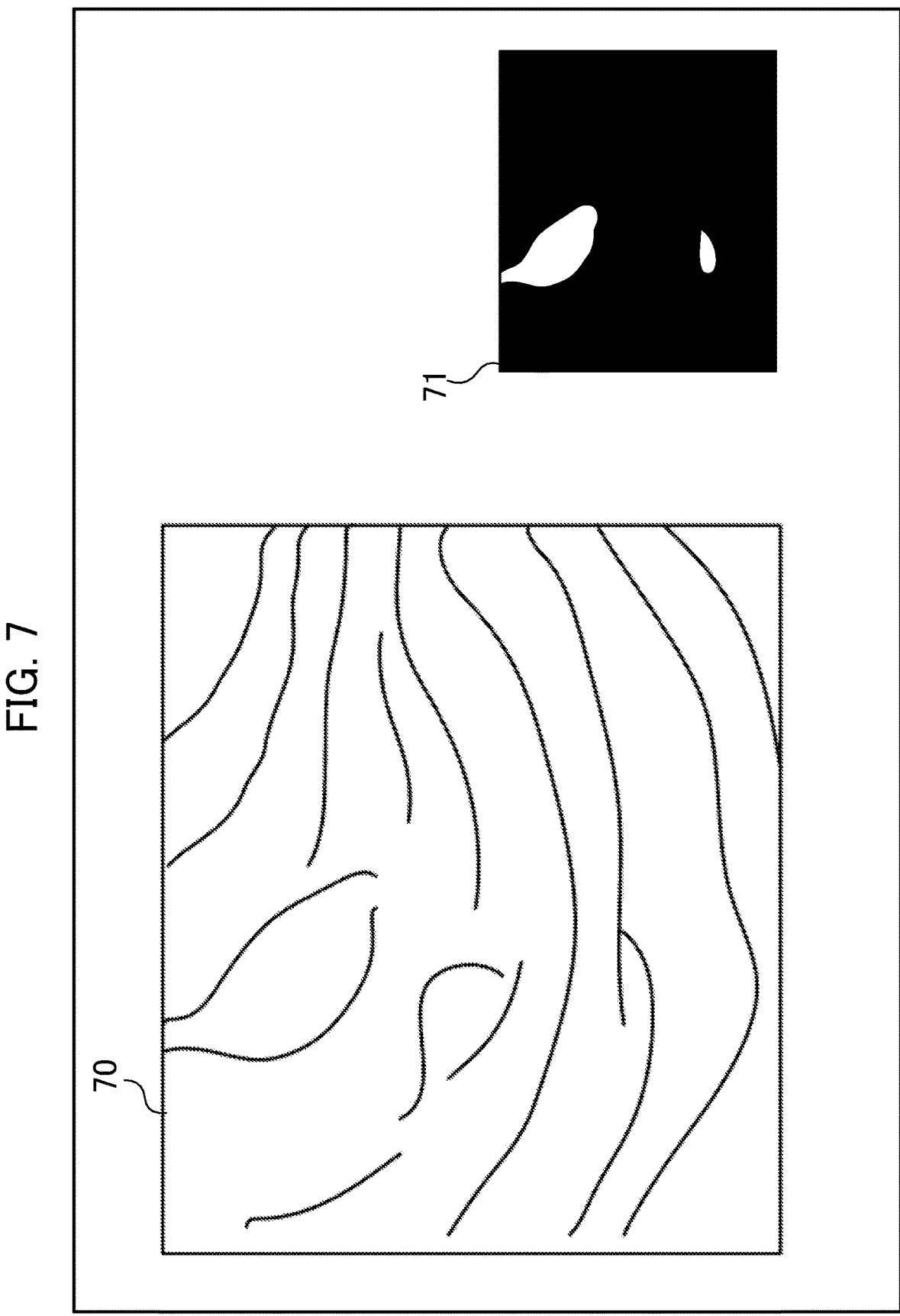
FIG. 7 It illustrates a display example of the display screen image displayed on a display device in an endoscopic inspection.

FIG. 7 shows a display example of a display screen image displayed by the display device 2 in the endoscopic inspection. The display control unit 35 of the image processing device 1 transmits the display information Ib generated on the basis of the captured images Ia acquired by the captured image acquisition unit 30 and the region extraction result Re generated by the region extraction unit 34 to the display device 2, and displays the display screen image shown in FIG. 7 on the display device 2.

In the example shown in FIG. 7, the display control unit 35 of the image processing device 1 provides on the display screen image a latest image display field 70 in which the most recently captured image Ia captured by the captured image acquisition unit 30 is displayed and a lesion part display field 71 in which a mask image with clear indication of the lesion image region Tc based on the region extraction result Re is displayed. In this instance, the lesion candidate segment detection unit 32 detects the lesion candidate segment St, and the image selection unit 33 determines whether or not the applicable condition of the segmentation model based on the confidence score or the feature vector is satisfied and selects the segmentation target image Itag accordingly. Then, the region extraction unit 34 extracts the lesion image region Tc by applying the segmentation model to the selected segmentation target image Itag, and the display control unit 35 displays a mask image representing the lesion image region Tc extracted by the region extraction unit 34 on the lesion part display field 71. The display control unit 35 displays a moving image based on the latest captured image Ia acquired by the captured image acquisition unit 30 on the latest image display field 70.

In this way, the display control unit 35 presents the corresponding lesion image region Tc together with the most recently captured image Ia, which suitably supports the inspector to grasp the lesion part.

In the display example shown in FIG. 7, the display control unit 35 may highlight the detected lesion image region Tc on the latest captured image Ia, without providing both of the latest image display field 70 and the lesion part display field 71, or with providing both of the latest image display field 70 and the lesion part display field 71. In this case, for example, the display control unit 35 may highlight the lesion image region Tc by adding an edging effect on the edge portion of the lesion image region Tc on the captured image Ia to be displayed, or may highlight the lesion image region Tc by setting pixel values of the whole lesion image region Tc on the captured image Ia to a predetermined value. Further, the display control unit 35 may display a reliability map representing the reliability as to whether or not each pixel corresponds to the lesion image region Tc, instead of displaying the mask image of the lesion image region Tc on the lesion part display field 71.

Next, a description will be given of the update timing of the image to be displayed on the lesion part display field 71.

A description will be given of such a case that the lesion candidate segment St is continued after the display of the image of the lesion image region Tc in the lesion part display field 71 and that the image selection unit 33 newly selects the segmentation target image Itag and that the region extraction unit 34 generates the region extraction result Re. In this case, the display control unit 35 updates the display of the lesion part display field 71 by an image representing the lesion image region Tc based on the newly generated region extraction result Re. Thus, the display control unit 35 can suitably update the display of the lesion part display field 71, based on the most recent segmentation target image Itag selected by the image selection unit 33.

Here, when the region extraction unit 34 generates the region extraction result Re in response to the selection of a new segmentation target image Itag by the image selection unit 33, the display control unit 35 may determine whether or not to update the display of the lesion part display field 71 based on the area of the lesion image region Tc. Specifically, if the area of the lesion image region Tc represented by the newly generated region extraction result Re is larger than the area (i.e., the number of pixels to form the lesion image region Tc) of the lesion image region Tc ongoingly displayed in the lesion part display field 71, the display control unit 35 updates the display of the lesion part display field 71 based on the newly generated region extraction result Re. As described above, if multiple segmentation target images Itag are selected in a single lesion candidate segment St, the display control unit 35 determines the segmentation target image Itag to be used for displaying the lesion image region Tc, on the basis of the area of the lesion image region Tc. In this way, the display control unit 35 can display an image suitably representing the lesion part on the lesion part display field 71.

Further, if the newest captured image Ia does not belong to the ongoing lesion candidate segment St, the display control unit 35 may stop displaying the image in the lesion part display field 71. In this case, if the display control unit 35 detects, based on the segment detection result Rd generated by the lesion candidate segment detection unit 32, that the lesion candidate segment St has ended, the display control unit 35 hides the image being displayed on the lesion part display field 71. Thus, the display control unit 35 suitably suppresses continuing to display an image clearly showing the lesion part which is not the photographing target by the endoscope 3 anymore.

If the display control unit 35 detects a predetermined input based on the operation to the input unit 14 by the inspector, the display control unit 35 may stop updating the display of the image in the lesion part display field 71. In this case, the display control unit 35 continues (fixes) the display of the image displayed on the lesion part display field 71 at the time of detecting a predetermined input based on the operation to the input unit 14 by the inspector. Then, if the display control unit 35 detects a predetermined input to allow updating of the display of the image in the lesion part display field 71, the display control unit 35 resumes updating of the display of the image in the lesion part display field 71. Thus, the display control unit 35 stops the updating of the display relating to the lesion image region Tc in response to an external input based on the operation to the input unit 14 by the inspector. Thereby, the display control unit 35 can let the inspector confirm the display relating to the lesion image region Tc with an enough time.

(7) Processing Flow

Figure 8:
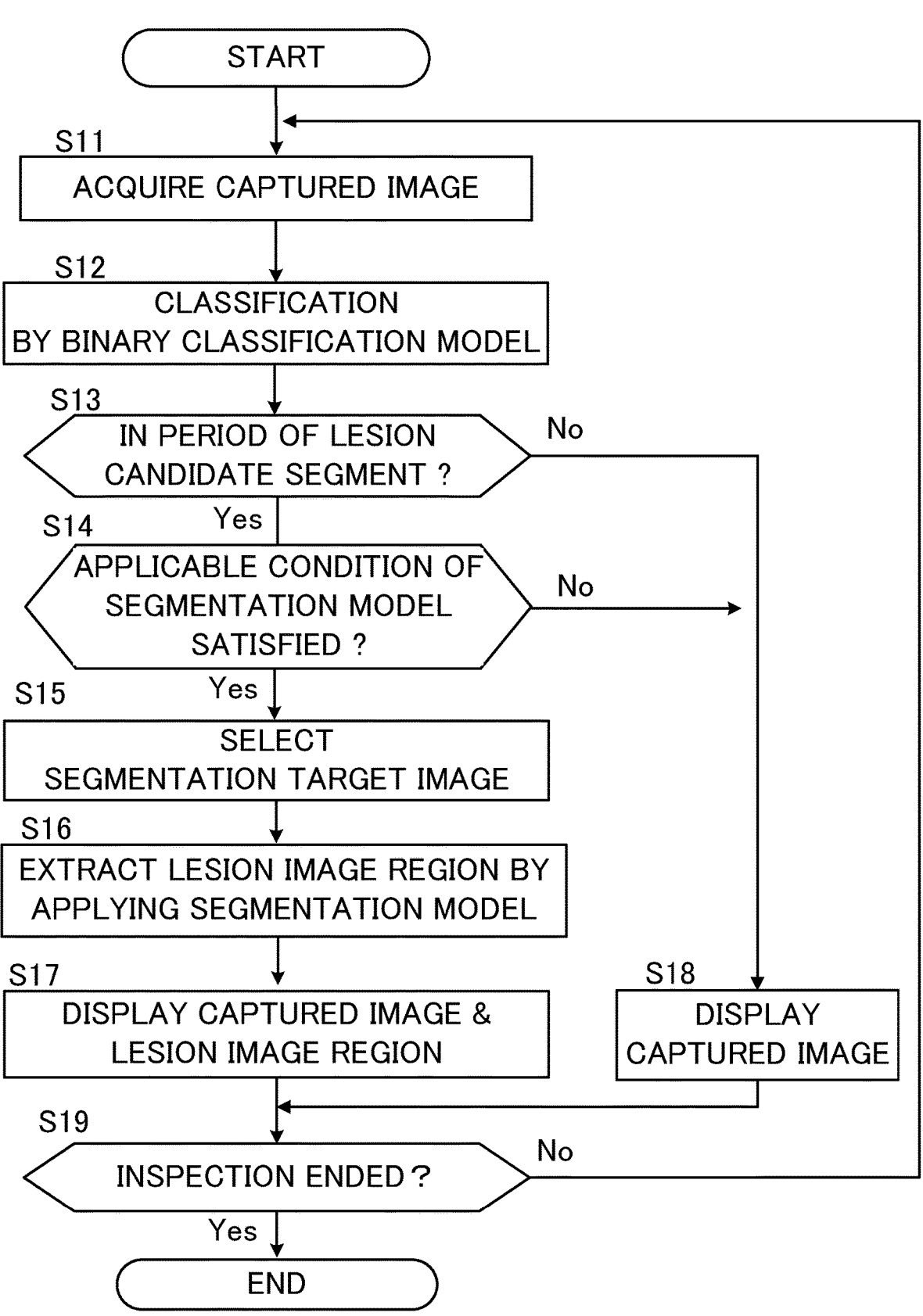
FIG. 8 It is an example of a flowchart showing an outline of a display process performed by the image processing device during the endoscopic inspection in the first example embodiment.

FIG. 8 is an example of a flowchart illustrating an outline of a process that is executed by the image processing device 1 during the endoscopic inspection in the first example embodiment.

First, the captured image acquisition unit 30 of the image processing device 1 acquires a captured image Ia (step S11). In this case, the captured image acquisition unit 30 of the image processing device 1 receives a captured image Ia from the endoscope 3 via the interface 13.

Next, the classification unit 31 of the image processing device 1 classifies the captured image Ia acquired at step S11 by the binary classification model configured on the basis of the binary classification model information D1 (step S12). The lesion candidate segment detection unit 32 of the image processing device 1 determines, based on the classification result Rc generated by the classification unit 31, whether or not it is in the period of the lesion candidate segment St (step S13). Then, if it is in the period of the lesion candidate segment St (step S13; Yes), the process proceeds to step S14. On the other hand, if it is not in the period of the lesion candidate segment St (step S13; No), the display control unit 35 displays the captured image Ia acquired at step S11 on the display device 2 (step S18). The display control unit 35 may erase the display relating to the lesion image region Tc, if the display control unit 35 is in the middle of executing the display relating to the lesion image region Tc based on step S17 to be described later.

On the other hand, if it is in the period of the lesion candidate segment St, the image selection unit 33 of the image processing device 1 determines whether or not the applicable condition of the segmentation model is satisfied (step S14). In this case, for example, the image selection unit 33 determines whether or not the applicable condition of the segmentation model based on at least one of the confidence score or the feature vector described in the section "(5) Selection of Segmentation Target Image" is satisfied. If it is determined that the applicable condition of the segmentation model is satisfied (step S14; Yes), the image selection unit 33 selects the segmentation target image Itag (step S15). In this instance, the image selection unit 33 may select the most recently captured image Ia as the segmentation target image Itag or may select the segmentation target image Itag on the basis of the confidence score of the presence of a lesion part. Then, the region extraction unit 34 extracts the lesion image region Tc by applying the segmentation model built on the basis of the segmentation model information D2 to the segmentation target image Itag (step S16). Then, the display control unit 35 causes the display device 2 to execute the display of the most recently captured image Ia and the display relating to the lesion image region Tc extracted at step S16 (step S17).

After the process at step S17 or the process at step S18, the image processing device 1 determines whether or not the endoscopic inspection is completed (step S19). For example, the image processing device 1 determines that the endoscopic inspection has been completed, if a predetermined input or the like to the input unit 14 or the operation unit 36 is detected. If it is determined that the endoscopic inspection has been completed (step S19; Yes), the image processing device 1 ends the process of the flowchart. On the other hand, if it is determined that the endoscopic inspection has not been completed (step S19; No), the image processing device 1 gets back to the process at step S11. Then, the image processing device 1 performs processes at step S11 to step S19 on a captured image Ia newly generated by the endoscope 3.

(8) Modifications

Next, modifications suitable for the above-described example embodiment will be described. The following modifications may be applied to the example embodiments described above in any combination.

First Modification

The image processing device 1 may process, after the inspection, a video configured by captured images Ia that were generated during endoscopic inspection.

For example, when the video to be processed is designated based on a user input by the input unit 14 at any timing after the inspection, the image processing device 1 sequentially applies the procedure of the flowchart shown in FIG. 8 to the time series captured images Ia constituting the video. Then, the image processing device 1 ends the process of the flowchart when it is determined at step S19 that the video has ended. In contrast, if the video has not ended, the image processing device 1 gets back to the process at step S11 to continue the process of the flowchart for the subsequent captured image Ia.

Second Modification

The binary classification model information D1 and the segmentation model information D2 may be stored in a storage device provided separately from the image processing device 1.

Figure 9:
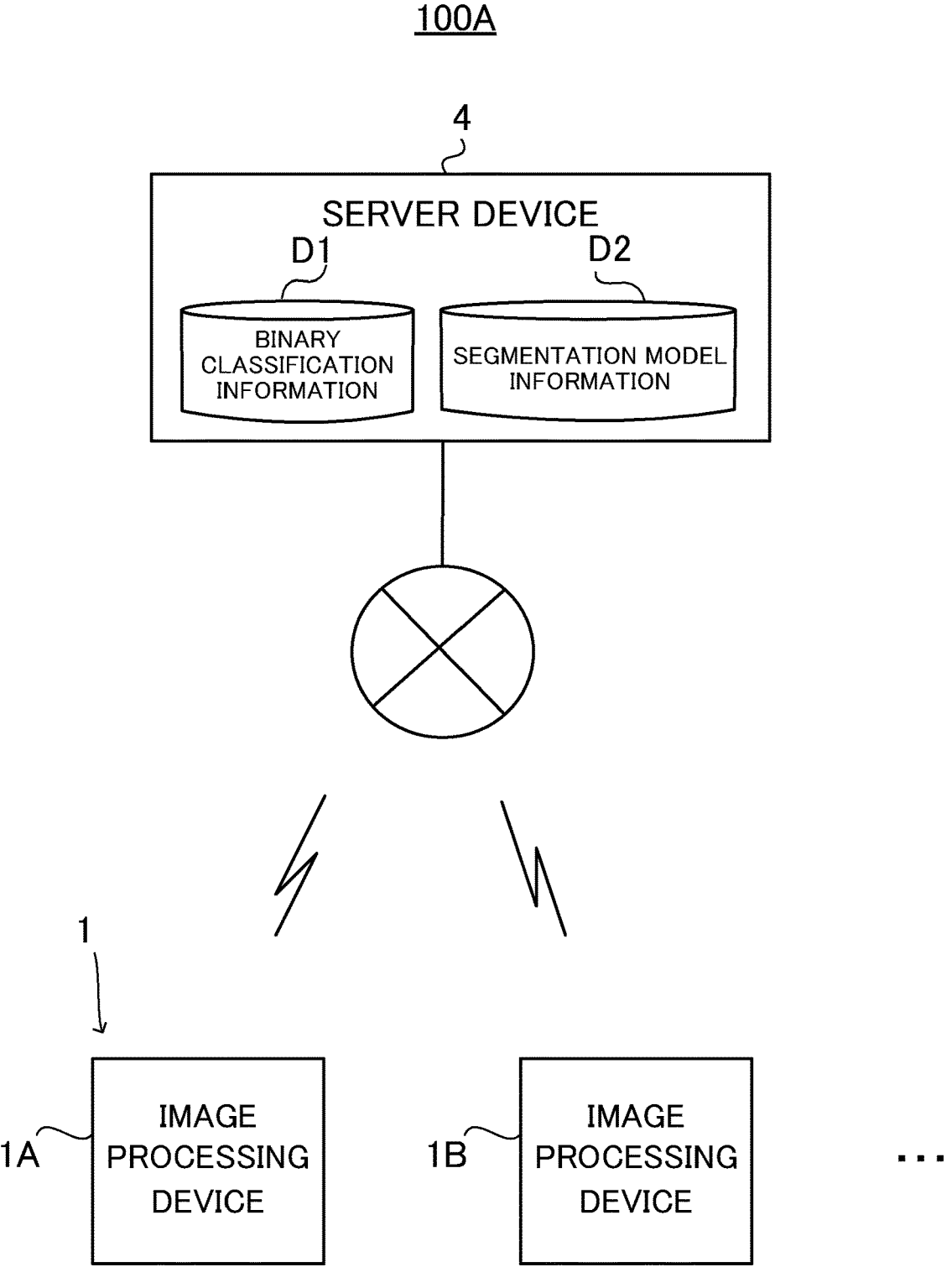
FIG. 9 It is a schematic configuration diagram of an endoscopic inspection system in a modification.

FIG. 9 is a schematic configuration diagram of an endoscopic inspection system 100A in the second modification. In FIG. 9, for simplicity, the display device 2 and the endoscope 3 and the like are not shown. The endoscopic inspection 100A shown in FIG. 9 includes a server is device 4 that stores the binary classification model information D1 and the segmentation model information D2. Further, the endoscopic inspection system 100A includes a plurality of image processing devices 1 (1A, 1B, . . . ) capable of data communication with the server device 4 via a network.

In this instance, each image processing device 1 refers to the binary classification model information D1 and the segmentation model information D2 via the network. In this case, the interface 13 of each image processing device 1 includes a communication interface such as a network adapter for performing data communication. In this configuration, each image processing device 1 refer to the binary value classification model information D1 and the segmentation model information D2 in the same manner as in the above-described example embodiment, and can suitably perform the extraction process and the display process regarding the lesion image region Tc

Third Modification

The detection target to be detected by the segmentation model is not limited to a lesion part, and it may be any attention part (point) that the inspector needs to notice. Examples of such an attention part include a lesion part, an inflammation part, a point with an operating mark or other cuts, a point with a fold or a protrusion, a point on the wall surface of the lumen where the pointed end unit 38 of the endoscope 3 tends to get contact (caught).

Fourth Modification

The image processing device 1 may use a classification model configured to perform classification into three or more classes, instead of the binary classification model. For example, the classification model to be used by the image processing device 1 may be a model configured to perform classification into "X+1" classes "first lesion type" to "Xth lesion type" ("X" is an integer of two or more) and "non-lesion". In this instance, the memory 12 stores the classification model information that is information regarding the classification model configured to perform classification into three or more classes, without storing the binary classification model information D1. The image processing device 1 generates the classification result for the captured image Ia by referring to the classification model information.

Thus, the classification model to be used by the image processing device may be a model configured to determine "presence or absence of a lesion", and is not limited to the binary classification model.

Second Example Embodiment

Figure 10:
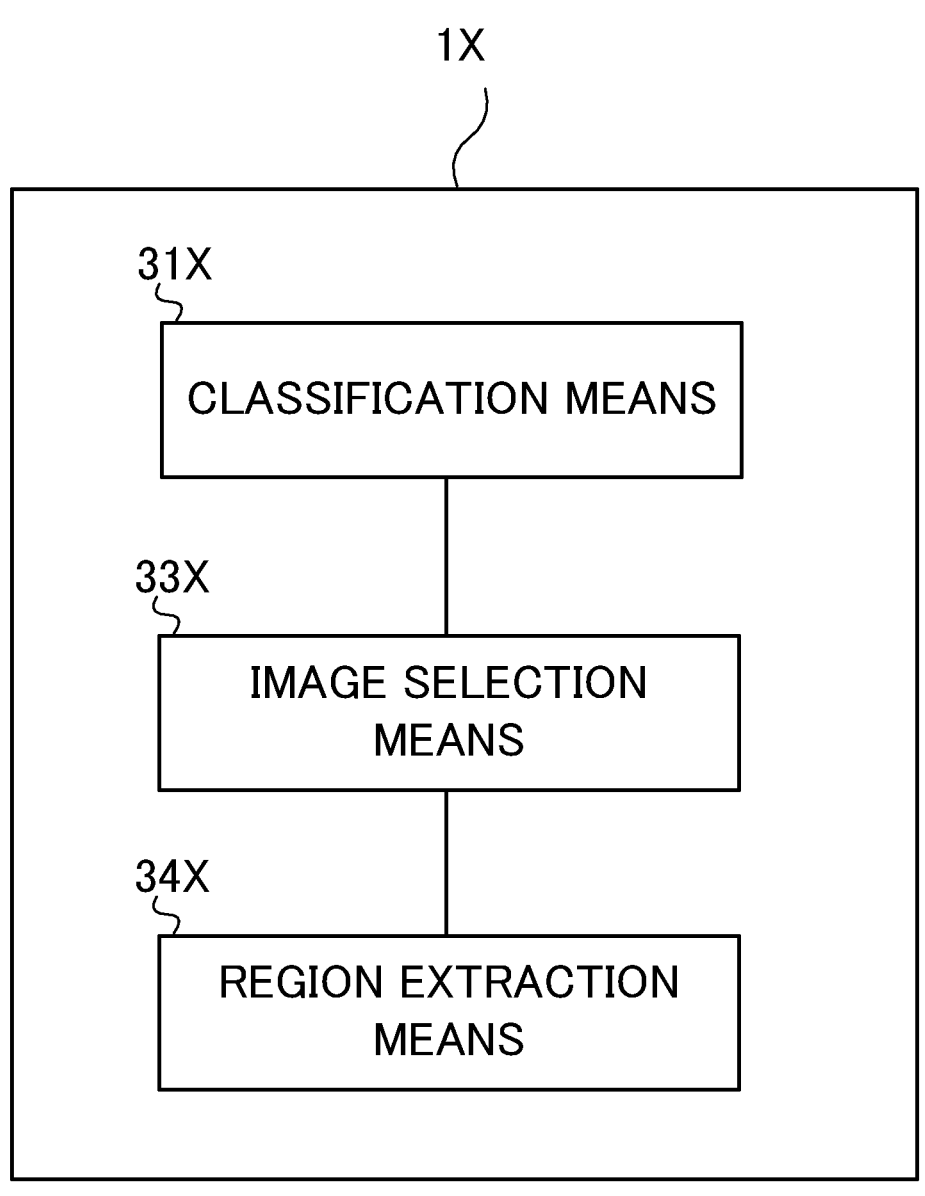
FIG. 10 It is a block diagram of the image processing device according to a second example embodiment.

FIG. 10 is a block diagram of an image processing device 1X according to the second example embodiment. The image processing device 1X includes a classification means 31X, an image selection means 33X, and a region extraction means 34X.

The classification means 31X is configured to classify each captured image acquired in time series by photographing an inspection target by a photographing unit provided in an endoscope, according to whether or not the each captured image includes an attention part to be paid attention to. Examples of the classification means 31X include the classification unit 31 in the first example embodiment (including modifications, the same shall apply hereinafter). The classification means 31X may immediately acquire the each captured image as soon as the photographing unit generates the each captured image, or may acquire, at a predetermined timing, the each captured image stored in the storage device generated by the photographing unit in advance.

The image selection means 33X is configured to select a target image to be subjected to extraction of a region of the attention part from the each captured image, based on a result of the classification. Examples of the image selection means 33X include the image selection unit 33 in the first example embodiment.

The region extraction means 34X is configured to extract the area of the attention part from the target image. Examples of the region extraction means 34X include the region extraction unit 34 in the first example embodiment.

Figure 11:
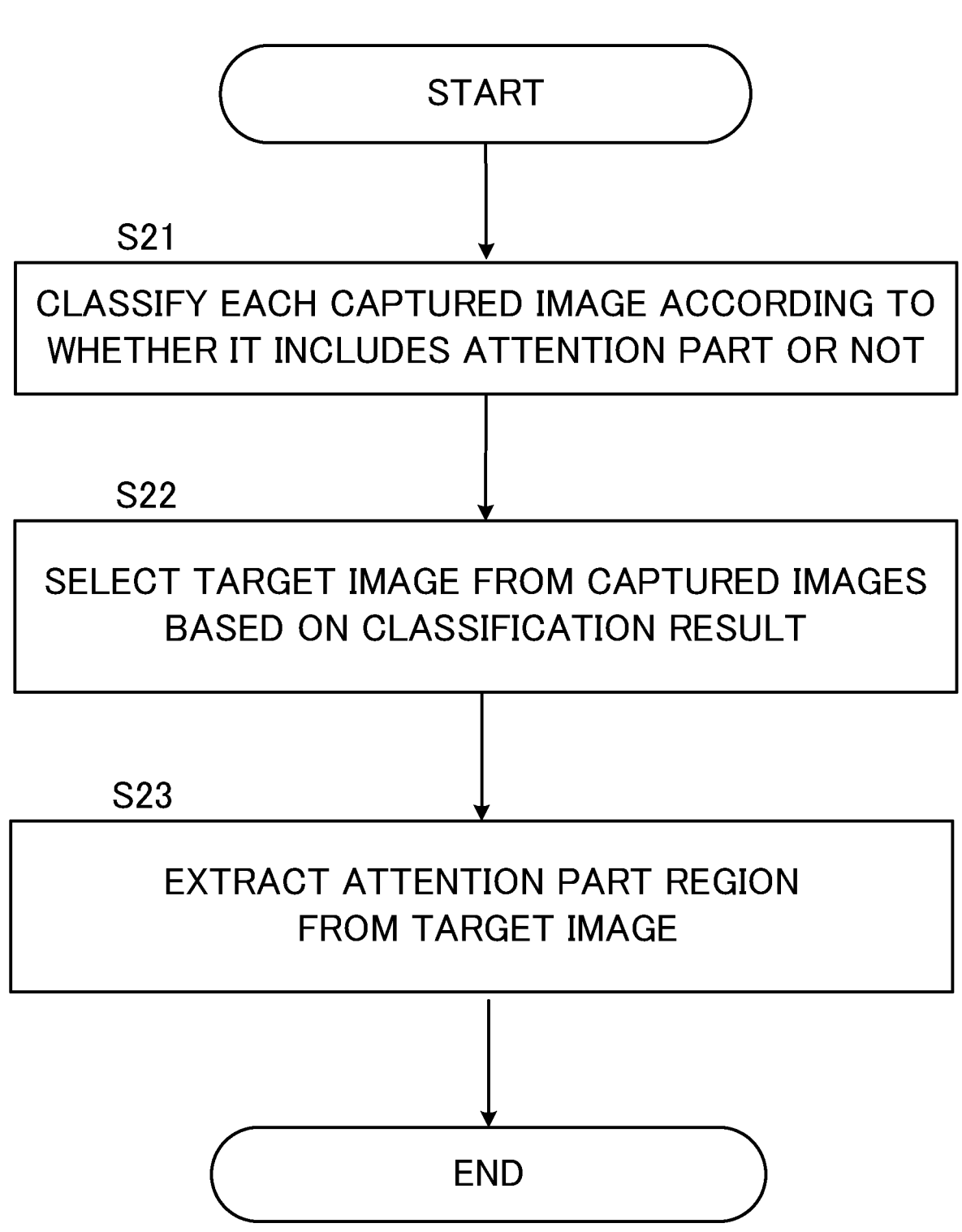
FIG. 11 It is an example of a flowchart executed by the image processing device in the second example embodiment.

FIG. 11 is an example of a flowchart showing a processing procedure in the second example embodiment. First, the classification means 31X classifies each captured images acquired in time series by photographing an inspection target by a photographing unit provided in an endoscope, according to whether or not the each captured image includes an attention part to be paid attention to (step S21). Next, the image selection means 33X selects a target image to be subjected to extraction of a region of the attention part from the each captured image, based on a result of the classification (step S22). Then, the region extraction means 34X extracts the region of the attention part from the target image (step S23).

According to the second example embodiment, the image processing device 1X limits the target image of extraction of an attention part region based on the classification result as to whether or not each image includes an attention part. Thereby, it is possible to suitably extract the attention part region while reducing the processing load.

The whole or a part of the example embodiments described above (including modifications, the same applies hereinafter) can be described as, but not limited to, the following Supplementary Notes.

[Supplementary Note 1]

An image processing device comprising:

a classification means configured to classify each captured image acquired in time series by photographing an inspection target by a photographing unit provided in an endoscope, according to whether or not the each captured image includes an attention part to be paid attention to;

an image selection means configured to select a target image to be subjected to extraction of a region of the attention part from the each captured image, based on a result of the classification; and a region extraction means configured to extract the region of the attention part from the target image.

[Supplementary Note 2]

The image processing device according to Supplementary Note 1, wherein the image selection means is configured, if a condition regarding the result of the classification is satisfied consecutively for a predetermined number of captured images in the time series, to select the target image from the predetermined number of the captured images.

[Supplementary Note 3]

The image processing device according to Supplementary Note 1 or 2, wherein the classification means is configured to classify the each captured image acquired in time series, based on a classification model configured to output, when an image is inputted thereto, information regarding presence or absence of the attention part in the image.

[Supplementary Note 4]

The image processing device according to Supplementary Note 3, wherein the classification model is configured to output a confidence score regarding the presence or absence of the attention part, and wherein the image selection means is configured to select the target image based on the confidence score.

[Supplementary Note 5]

The image processing device according to Supplementary Note 4, wherein the image selection means is configured, if a condition regarding the confidence score is satisfied consecutively for a predetermined number of captured images in the time series, to select the target image from the predetermined number of the captured images.

[Supplementary Note 6]

The image processing device according to any one of Supplementary Notes 1 to 5, wherein the classification means is configured to perform feature extraction of the each captured image, and wherein the image selection means is configured to select the target image based on feature vectors obtained by the feature extraction.

[Supplementary Note 7]

The image processing device according to Supplementary Note 6, wherein the image selection means is configured, if a condition regarding a similarity of a predetermined number of consecutive captured images in the time series is satisfied, to select the target image from the predetermined number of the captured images, the similarity being calculated by the feature vectors.

[Supplementary Note 8]

The image processing device according to any one of Supplementary Notes 2, 5, and 7, wherein the image selection means is configured to change the predetermined number after selecting the target image, during a time segment in which consecutive captured images classified as presence of the attention part are acquired.

[Supplementary Note 9]

The image processing device according to any one of Supplementary Notes 1 to 8, wherein the region extraction means is configured to extract the region of the attention part from the target image, based on a segmentation model that is a model configured to output, when an image is inputted to the model, information regarding the region of the attention part in the inputted image.

[Supplementary Note 10]

The image processing device according to any one of Supplementary Notes 1 to 9, further comprising a display control means configured to display information regarding the region of the attention part on a display device.

[Supplementary Note 11]

The image processing device according to Supplementary Note 10, wherein, if plural target images are selected during a time segment in which consecutive captured images classified as including the attention part are acquired, the display control means is configured to determine, based on area of the region of the attention part, the target image to be used for display the information regarding the region of the attention part.

[Supplementary Note 12]

The image processing device according to Supplementary Note 10 or 11, wherein the display control means is configured to stop updating the display of the information regarding the region of the attention part, based on an external input.

[Supplementary Note 13]

An image processing method executed by a computer, the image processing method comprising:

classifying each captured image acquired in time series by photographing an inspection target by a photographing unit provided in an endoscope, according to whether or not the each captured image includes an attention part to be paid attention to;

selecting a target image to be subjected to extraction of a region of the attention part from the each captured image, based on a result of the classification; and extracting the region of the attention part from the target image.

[Supplementary Note 14]

A storage medium storing a program executed by a computer, the program causing the computer to:

classify each captured image acquired in time series by photographing an inspection target by a photographing unit provided in an endoscope, according to whether or not the each captured image includes an attention part to be paid attention to;

select a target image to be subjected to extraction of a region of the attention part from the each captured image, based on a result of the classification; and extract the region of the attention part from the target image.

While the invention has been particularly shown and described with reference to example embodiments thereof, the invention is not limited to these example embodiments. It will be understood by those of ordinary skilled in the art that various changes in form and details may be made therein without departing from the spirit and scope of the present invention as defined by the claims. In other words, it is needless to say that the present invention includes various modifications that could be made by a person skilled in the art according to the entire disclosure including the scope of the claims, and the technical philosophy. All Patent and Non-Patent Literatures mentioned in this specification are incorporated by reference in its entirety.

DESCRIPTION OF REFERENCE NUMERALS 1, 1X Image processing device
2 Display device
3 Endoscope
4 Server device
11 Processor
12 Memory
13 Interface
14 Input unit
15 Light source unit
16 Sound output unit
100, 100A Endoscopic inspection system

What is claimed is:

1. An image processing device comprising:

at least one memory configured to store instructions; and at least one processor configured to execute the instructions to:

classify each captured image acquired in time series by photographing an inspection target by a photographing unit provided in an endoscope, according to whether or not the each captured image includes an attention part to be paid attention to based on a classification model, wherein the classification model is trained by machine learning to output information regarding presence or absence of the attention part in the image in case where an image is inputted to the classification model, and wherein the classification model is configured to output a confidence score regarding the presence or absence of the attention part;

in a case where a condition regarding the confidence score is satisfied consecutively for a predetermined number of captured images in the time series, select a target image to be subjected to extraction of a region of the attention part from the predetermined number of the captured images, based on the confidence score; and extract the region of the attention part from the target image.

2. The image processing device according to claim 1, wherein the at least one processor is configured to execute the instructions, in a case where a condition regarding the result of the classification is satisfied consecutively for a predetermined number of captured images in the time series, to select the target image from the predetermined number of the captured images.

3. The image processing device according to claim 2, wherein the at least one processor is configured to execute the instructions to change the predetermined number after selecting the target image, during a time segment in which consecutive captured images classified as presence of the attention part are acquired.

4. The image processing device according to claim 1, wherein the at least one processor is configured to execute the instructions to perform feature extraction of the each captured image, and wherein the at least one processor is configured to execute the instructions to select the target image based on feature vectors obtained by the feature extraction.

5. The image processing device according to claim 4, wherein the at least one processor is configured to execute the instructions, in a case where a condition regarding a similarity of a predetermined number of consecutive captured images in the time series is satisfied, to select the target image from the predetermined number of the captured images, the similarity being calculated by the feature vectors.

6. The image processing device according to claim 1, wherein the at least one processor is configured to execute the instructions to extract the region of the attention part from the target image, based on a segmentation model that is a model configured to output, when an image is inputted to the model, information regarding the region of the attention part in the inputted image.

7. The image processing device according to claim 1, wherein the at least one processor is configured to further execute the instructions to display information regarding the region of the attention part on a display device.

8. The image processing device according to claim 7, wherein, in a case where plural target images are selected during a time segment in which consecutive captured images classified as including the attention part are acquired, the at least one processor is configured to execute the instructions to determine, based on area of the region of the attention part, the target image to be used for display the information regarding the region of the attention part.

9. The image processing device according to claim 7, wherein the at least one processor is configured to execute the instructions to stop updating the display of the information regarding the region of the attention part, based on an external input.

10. An image processing method executed by a computer, the image processing method comprising:

classifying each captured image acquired in time series by photographing an inspection target by a photographing unit provided in an endoscope, according to whether or not the each captured image includes an attention part to be paid attention to based on a classification model, wherein the classification model is trained by machine learning to output information regarding presence or absence of the attention part in the image in case where an image is inputted to the classification model, and wherein the classification model is configured to output a confidence score regarding the presence or absence of the attention part;

in a case where a condition regarding the confidence score is satisfied consecutively for a predetermined number of captured images in the time series, selecting a target image to be subjected to extraction of a region of the attention part from the predetermined number of the captured images, based on the confidence score; and extracting the region of the attention part from the target image.

11. The image processing method according to claim 10, the image processing method comprising:

in a case where a condition regarding the result of the classification is satisfied consecutively for a predetermined number of captured images in the time series, selecting the target image from the predetermined number of the captured images.

12. The image processing method according to claim 11, the image processing method comprising:

changing the predetermined number after selecting the target image, during a time segment in which consecutive captured images classified as presence of the attention part are acquired.

13. The image processing method according to claim 10, the image processing method comprising:

performing feature extraction of the each captured image, and selecting the target image based on feature vectors obtained by the feature extraction.

14. The image processing method according to claim 13, the image processing method comprising:

in a case where a condition regarding a similarity of a predetermined number of consecutive captured images in the time series is satisfied, selecting the target image from the predetermined number of the captured images, the similarity being calculated by the feature vectors.

15. The image processing method according to claim 10, the image processing method comprising:

extracting the region of the attention part from the target image, based on a segmentation model that is a model configured to output, when an image is inputted to the model, information regarding the region of the attention part in the inputted image.

16. The image processing method according to claim 10, the image processing method comprising:

displaying information regarding the region of the attention part on a display device.

17. The image processing method according to claim 16, the image processing method comprising:

in a case where plural target images are selected during a time segment in which consecutive captured images classified as including the attention part are acquired, determining, based on area of the region of the attention part, the target image to be used for display the information regarding the region of the attention part.

18. The image processing method according to claim 16, the image processing method comprising:

stopping updating the display of the information regarding the region of the attention part, based on an external input.

19. A non-transitory computer readable storage medium storing a program executed by a computer, the program causing the computer to:

classify each captured image acquired in time series by photographing an inspection target by a photographing unit provided in an endoscope, according to whether or not the each captured image includes an attention part to be paid attention to based on a classification model, wherein the classification model is trained by machine learning to output information regarding presence or absence of the attention part in the image in case where an image is inputted to the classification model, and wherein the classification model is configured to output a confidence score regarding the presence or absence of the attention part;

in a case where a condition regarding the confidence score is satisfied consecutively for a predetermined number of captured images in the time series, select a target image to be subjected to extraction of a region of the attention part from the predetermined number of the captured images, based on the confidence score; and extract the region of the attention part from the target image.

* * * * *